United States Patent [19]

Neri et al.

[11] Patent Number: 4,474,813

[45] Date of Patent: * Oct. 2, 1984

[54] PHARMACEUTICAL PREPARATIONS COMPRISING FLUTAMIDE

[75] Inventors: Rudolph O. Neri, Hawthorne, N.J.; John G. Topliss, Ann Arbor, Mich.

[73] Assignee: Schering Corporation, Kenilworth, N.J.

[ * ] Notice: The portion of the term of this patent subsequent to May 11, 1999 has been disclaimed.

[21] Appl. No.: 381,084

[22] Filed: May 24, 1982

Related U.S. Application Data

[60] Continuation of Ser. No. 200,108, Oct. 24, 1980, abandoned, and a continuation-in-part of Ser. No. 725,821, Sep. 23, 1976, Pat. No. 4,329,364, which is a division of Ser. No. 505,116, Sep. 11, 1974, Pat. No. 3,995,060, which is a continuation-in-part of Ser. No. 264,655, Jun. 20, 1972, abandoned, which is a continuation-in-part of Ser. No. 146,461, May 24, 1971, abandoned, which is a continuation-in-part of Ser. No. 876,999, Nov. 14, 1969, abandoned, which is a continuation-in-part of Ser. No. 734,854, Jun. 6, 1968, abandoned, which is a continuation-in-part of Ser. No. 573,836, Aug. 22, 1966, abandoned.

[51] Int. Cl.$^3$ .......................................... A61K 31/165
[52] U.S. Cl. .................................................... 424/324
[58] Field of Search ......................................... 424/324

[56] References Cited

U.S. PATENT DOCUMENTS

| | | | |
|---|---|---|---|
| 3,407,056 | 10/1968 | Schwartz | 71/118 |
| 3,426,049 | 2/1969 | Baker et al. | 260/404 |
| 3,995,060 | 11/1976 | Neri et al. | 424/324 |
| 4,329,364 | 5/1982 | Neri et al. | 424/324 |

OTHER PUBLICATIONS

Baker et al., J. of Med. Chem., vol. 10, No. 1, Jan. 1967, pp. 93–95.

Primary Examiner—Jerome D. Goldberg
Attorney, Agent, or Firm—Paul H. Ginsburg; Bruce M. Eisen; Mary S. King

[57] ABSTRACT

A pharmaceutical preparation comprising flutamide, useful in the treatment of prostatic carcinoma, is disclosed.

7 Claims, No Drawings

PHARMACEUTICAL PREPARATIONS COMPRISING FLUTAMIDE

This is a continuation of application Ser. No. 200,108, filed Oct. 24, 1980, now abandoned, and a continuation-in-part of our copending application Ser. No. 725,821, filed Sept. 23, 1976, now U.S. Pat. No. 4,329,364; which is, in turn, a division of application Ser. No. 505,116, filed Sept. 11, 1974, now U.S. Pat. No. 3,995,060 which, in turn, is a continuation-in-part of our copending application Ser. No. 264,655, filed June 20, 1972 (now abandoned) which, in turn, is a continuation-in-part of application Ser. No. 146,461, filed May 24, 1971 (now abandoned), which, in turn, is a continuation-in-part of application Ser. No. 876,999, filed Nov. 14, 1969 (now abandoned), which, in turn, is a continuation-in-part of application Ser. No. 734,854, filed June 6, 1968 (now abandoned), which, in turn, is a continuation-in-part of application Ser. No. 573,836, filed Aug. 22, 1966 (now abandoned).

The present invention relates to pharmaceutical preparations comprising 4'-nitro-3'-trifluoromethylisobutyranilide. The USAN has approved the generic name "flutamide" for this compound, and this name will be used hereinafter. The preparation of flutamide is disclosed in U.S. Pat. No. 3,995,060, the disclosure of which is hereby incorporated herein by reference.

More specifically, the present invention relates to a pharmaceutical preparation in a dosage unit form adapted for systemic administration, useful in the treatment of prostate carcinoma, comprising a therapeutically effective quantity of flutamide together with a pharmaceutically acceptable carrier.

Numerous studies have shown that the preparations of the present invention are useful in the treatment of prostatic carcinoma. The preparations of the present invention may also be used to treat other androgen dependent carcinomas.

It will be understood by the prescribing clinician that carcinomas are complex and difficult conditions to treat and that no single treatment will necessarily be effective in curing a particular patient. However, in view of the severity of the condition involved, the relative absence of serious side effects for effective dosages of flutamide, and the possibility of achieving at least an ameliorative effect, the preparations of the present invention are useful in this context.

In the treatment of prostatic carcinoma, the compositions of the present invention should provide a quantity of flutamide equivalent to a dose of about 2 to 3 mg per kg of body weight per day, preferably about 4 to about 20 mg per kg of body weight per day, more preferably about 7 to 14 mg per kg of body weight per day. The aforementioned doses may be divided into two or more portions for administration over the course of the day, for example, one-third of the daily dose administered three times per day. Pharmaceutical preparations for a 70 kilogram mammal should provide a daily dose of flutamide of about 100 mg to about 2000 mg, preferably about 250 mg to about 1500 mg, and more preferably about 500 mg to about 1000 mg, and should be continued until symptomatic relief is obtained, as ascertained by the attending diagnostician.

The pharmaceutical preparations of this invention include such oral dosage forms as tablets, capsules and elixirs as well as parenteral dosage forms, e.g. ampuls and vials.

Additionally, they may be in the form of suppositories (both rectal and urethral). In tablet form flutamide is compounded with an inert pharmaceutical carrier which may contain a suitable binder such as, for example, gums, starches, and sugars. The ingredients may also be incorporated into gelatin capsules or formulated into elixirs which have the advantage of being susceptible to manipulations in flavor by the addition of standard natural or synthetic flavoring agents. Highly satisfactory administration may also be achieved in the form of aqueous parenteral suspension.

Preferably, the aforementioned formulations are so proportioned as to afford a unit dose of about 125 or about 250 mg of flutamide. Thus, for example, a preferred dosage of 750 mg per day could thus be administered as one 250 mg tablet or capsule three times per day or two 125 mg tablets or capsules three times per day.

Representative flutamide formulations are as follows:

| TABLET FORMULATION | |
|---|---|
| Ingredients | Milligrams per Tablet |
| Flutamide | 250.00 |
| Lactose, anhydrous | 221.70 |
| Sodium lauryl sulfate | 15.00 |
| Microcrystalline cellulose | 100.00 |
| Starch | 162.50 |
| Water (evaporates) | (0.29) |
| Silica Gel (Syloid 244) | 0.40 |
| Magnesium stearate | 0.40 |
| Tablet Weight | 750.00 |

Blend the above ingredients using a wet granulation method and compress into tablets using standard techniques.

| PARENTERAL SUSPENSION FORMULATION | |
|---|---|
| Ingredients | Milligrams per Milliliter |
| Flutamide | 250.00 |
| Methyl Cellulose 15 cps. U.S.P. | 0.25 |
| Sodium Citrate, Dihydrate | 30.00 |
| Benzyl Alcohol, NF | 9.00 |
| Methylparaben, U.S.P. | 1.80 |
| Propylparaben, U.S.P. | 1.20 |
| Water for Injection, U.S.P. q.s. a.d. | 1.00 |

Using standard techniques, combine the above ingredients to prepare a parenteral suspension.

| CAPSULE FORMULATION | | | |
|---|---|---|---|
| Ingredients | Milligrams/Capsule | | |
| Flutamide | 125 | 250 | 200 |
| Lactose, hydrous, USP | 360.5 | 235.5 | 185 |
| Sodium Lauryl Sulfate, NF | 12 | 12 | 12 |
| Povidone, USP (Polyvinylpyrrolidone) | 25 | 25 | 25 |
| Water, Purified, USP (evap.) or S.D. Alcohol, 3-A (evap.)* | — | — | — |
| Corn Starch (Food Grade) | 77 | 77 | 77 |
| Magnesium Stearate, NF | 0.5 | 0.5 | 1.0 |
| Fill Weight (mg.) | 600 | 600 | 500 |

*Approximately 75 ml. 3-A alcohol/100 capsules, or 60 ml. water/1000 capsules.

Blend the above by standard techniques and fill into capsules.

We claim:

1. A pharmaceutical preparation in the form of a tablet, capsule, or suppository, adapted for systemic administration to obtain a therapeutic effect against prostatic carcinoma, comprising a therapeutically effective quantity of flutamide together with a pharmaceutically acceptable carrier suitable for systemic administration.

2. A preparation according to claim 1, in the form of a capsule.

3. A preparation according to claim 1, in the form of a tablet.

4. A preparation according to claim 1, in the form of a suppository.

5. A pharmaceutical preparation in the form of an elixir, adapted for systemic administration to obtain a therapeutic effect against prostatic carcinoma, comprising a therapeutically effective quantity of flutamide together with a pharmaceutically acceptable flavoring agent.

6. A pharmaceutical product in parenteral form, adapted for systemic administration to obtain a therapeutic effect against prostatic carcinoma, comprisng a therapeutically effective quantity of flutamide together with water suitable for parenteral injection.

7. A pharmaceutical preparation in solid oral dosage form adapted for systemic administration to obtain a therapeutic effect against prostatic carcinoma, comprising a therapeutically effective quantity of flutamide together with a pharmaceutically acceptable excipient.

* * * * *